United States Patent [19]
Martyniuk et al.

[11] Patent Number: 5,524,338
[45] Date of Patent: Jun. 11, 1996

[54] METHOD OF MAKING IMPLANTABLE MICROELECTRODE

[75] Inventors: Jerry Martyniuk, Portland; Scott S. Corbett, III, both of Portland, Oreg.; Gerald E. Loeb, Northridge, Calif.; Klaus Mewes, Lilburn, Ga.; W. Eugene Skiens, Wilsonville, Oreg.; John J. Stobie, Portland, Oreg.; Doris A. Beck, Beaverton, Oreg.

[73] Assignee: PI Medical Corporation, Portland, Oreg.

[21] Appl. No.: 362,806

[22] Filed: Dec. 22, 1994

Related U.S. Application Data

[60] Division of Ser. No. 136,650, Oct. 14, 1993, abandoned, which is a continuation-in-part of Ser. No. 46,658, Apr. 12, 1993, abandoned, which is a division of Ser. No. 781,494, Oct. 22, 1991, Pat. No. 5,201,903.

[51] Int. Cl.⁶ .................................................. H01R 43/00
[52] U.S. Cl. ............................................. 29/825; 128/642
[58] Field of Search ................................ 29/825; 128/642

[56] References Cited

U.S. PATENT DOCUMENTS

| | | | |
|---|---|---|---|
| 3,361,871 | 1/1968 | Brandt | 174/112 |
| 3,525,798 | 8/1970 | Forber | 174/26 |
| 3,706,838 | 12/1972 | Boult | 174/25 |
| 3,751,801 | 8/1973 | Praeger et al. | |
| 3,775,552 | 11/1973 | Schumacher | 174/105 |
| 3,826,244 | 7/1974 | Salcman et al. | 128/642 |
| 3,857,996 | 12/1974 | Hensen et al. | 174/113 |

(List continued on next page.)

FOREIGN PATENT DOCUMENTS

| | | |
|---|---|---|
| 1115352 | 12/1981 | Canada. |
| 1075562 | 10/1954 | France. |
| 2162472 | 7/1973 | France. |
| 654392 | 6/1951 | United Kingdom. |
| 2233596 | 1/1991 | United Kingdom. |

OTHER PUBLICATIONS

IBM Technical Disclosure Bulletin vol. 6, No. 8 Jan. 1964 pp. 13–14 by R. E. Johnston et al.
IEEE Transactions on Biomed Engr vol. BME–26 No. 5 May 1979, pp. 273–279 by G. Gross.
MWS Wire Industries Technical Date Sheet—Aug. 1990, pp. 12–15.
The Parylene Press, No. 17, Summer 1994, Publication of Specialty Coating Systems.
Klomp et al., "Fabrication of Large Arrays of Cortical Electrodes for Use in Man," 1977, pp. 347–364.
Gerald E. Loeb, M. D., "Neural prosthetic interfaces with the nervous system," May 1989, Trends in Neuroscience, vol. 12, No. 5, pp. 195–201 (1989).
Hugh S. Lusted, "In Vivo Electrical Stimulation Using Multichannel Photolithographic Electrode Arrays," Aug. 1986, IEEE Transactions on Biomedical Engineering, vol. BME–33, No. 8, pp. 800–803.

(List continued on next page.)

*Primary Examiner*—Carl J. Arbes
*Attorney, Agent, or Firm*—Chernoff, Vilhauer, McClung & Stenzel

[57] ABSTRACT

Microelectrodes for use in stimulating and detecting activity in neurons of living organisms, and a method of manufacturing such microelectrodes. An electrically conductive electrode core member is sharpened and coated with a thin layer of a dielectric material. An extremely small area of the core at the sharpened point is exposed by ablating the dielectric material by the use of ultraviolet laser beam scanned over the material. Multiconductor microelectrodes include multiple fine wires which may be arranged in helical strands, optionally supported by a central core member of stiffer material. Multiple conductors may also be supported within a tubular support such as a hollow needle whose distal end is cut at a slant to expose the conductors, or in flat ribbon configuration with openings in dielectric material defining active electrode sites. Multiple active electrode sites may be defined on a microelectrode accompanied by an integrated circuit after connection of the integrated circuit to a multiconductor cable.

12 Claims, 7 Drawing Sheets

U.S. PATENT DOCUMENTS

| | | | |
|---|---|---|---|
| 3,874,077 | 4/1975 | Folk . | |
| 3,881,246 | 5/1975 | Folk . | |
| 3,955,560 | 5/1976 | Stein et al. | 128/642 X |
| 4,132,858 | 1/1979 | Anderson et al. | 174/120 |
| 4,261,372 | 4/1981 | Hansen et al. | 128/784 |
| 4,284,841 | 8/1981 | Tijunelis et al. | 174/103 |
| 4,495,917 | 1/1985 | Byers | 128/419 |
| 4,503,124 | 3/1985 | Keane et al. | 428/372 |
| 4,532,930 | 8/1985 | Crosby et al. | 128/419 |
| 4,537,804 | 8/1985 | Keane et al. | 427/118 |
| 4,614,028 | 9/1986 | Rich | 29/749 |
| 4,640,983 | 2/1987 | Comte | 174/119 |
| 4,661,236 | 4/1987 | Gelo et al. | 29/825 X |
| 4,701,139 | 10/1987 | Good et al. | 439/497 |
| 4,800,236 | 1/1989 | Lemke | 174/36 |
| 4,804,337 | 2/1989 | Sebastien et al. | 439/449 |
| 4,809,712 | 3/1989 | Kuzma | 128/784 |
| 4,819,329 | 4/1989 | Haley et al. | 29/860 |
| 4,822,286 | 4/1989 | Bianca | 439/610 |
| 4,840,186 | 6/1989 | Lekholm et al. | 128/784 |
| 4,857,012 | 8/1989 | Yard | 439/471 |
| 4,964,414 | 10/1990 | Handa et al. | 128/784 |
| 4,969,706 | 11/1990 | Hardin et al. | 350/96.23 |
| 5,015,800 | 5/1991 | Vaupotic et al. | 174/34 |
| 5,056,531 | 10/1991 | Shimoyama | 128/784 |
| 5,067,903 | 11/1991 | Szyszkowski | 439/55 |
| 5,074,808 | 12/1991 | Beamenderfer et al. | 439/606 |
| 5,074,947 | 12/1991 | Estes et al. | 156/307 |
| 5,084,594 | 1/1992 | Cady et al. | 174/36 |
| 5,105,811 | 4/1992 | Kuzma | 128/420.6 |
| 5,111,812 | 5/1992 | Swanson et al. | 128/419 |
| 5,123,422 | 6/1992 | Charvin | 128/784 |
| 5,211,175 | 5/1993 | Gleason et al. | 128/642 |
| 5,220,130 | 6/1993 | Walters | 174/36 |
| 5,286,944 | 2/1994 | Li | 29/825 X |

OTHER PUBLICATIONS

Promotional Material, "Repair and Recoating of Parylene Coated Printed Circuit Boards," Specialty Coating Systems, Union Carbide, 1992, p. 10.

M. J. Mela "Microperforation with Laser Beam in the Preparation of Microelectrodes," 1966, IEEE Transactions on Biomedical Engineering, vol. BME–13, No. 2, pp. 70–76.

Gerald E. Loeb, et al., "Parylene as a Chronically Stable, Reproducible Microelectrode Insulator," 1977, IEEE Transactions on Biomedical Engineering, vol. BME–24, No. 2, pp. 121–128.

B. P. Levy, et al., "Definition of the Geometric Area of a Microelectrode Tip by Plasma Etching of Parylene, 1986, IEEE Transactions on Biomedical Engineering," vol. BME–33, No. 11, pp. 1046–1049.

S. J. Tanghe, et al., "A Planar IrO Multichannel Stimulating Electrode for Use in Neural Prostheses," 1990, pp. 464–467 (vol. B1, Sensors and Actuators).

K. Najafi, et al., "A High–Yield IC–Compatible Multichannel Recording Array," 1985, IEEE Transactions on Electron Devices, vol. ED–32, No. 7, pp. 1206–1211.

Gerald E. Loeb, M. D., "Progress Toward a Visual Prosthesis", Sep. 1991, pp. 1–11.

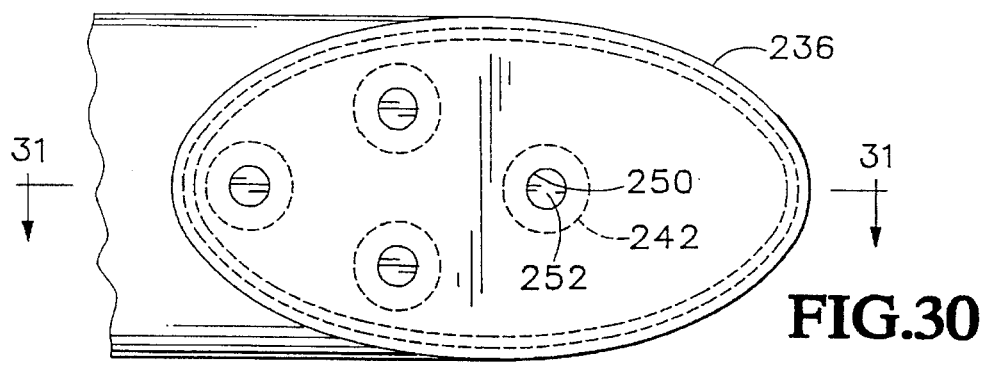
FIG.30
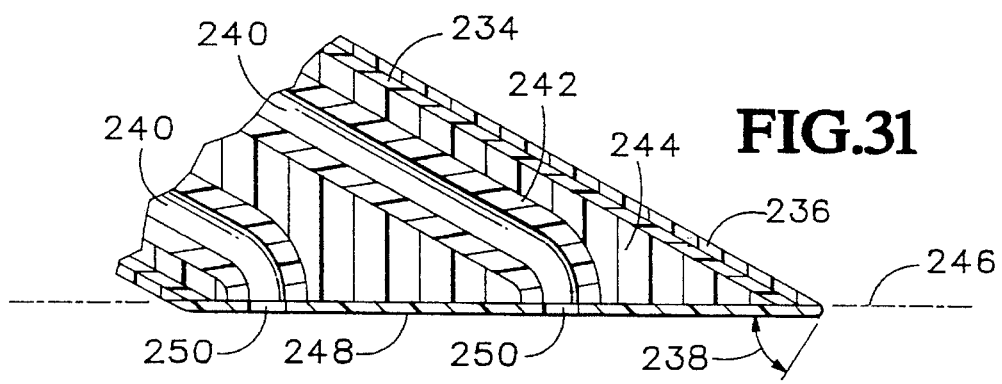
FIG.31
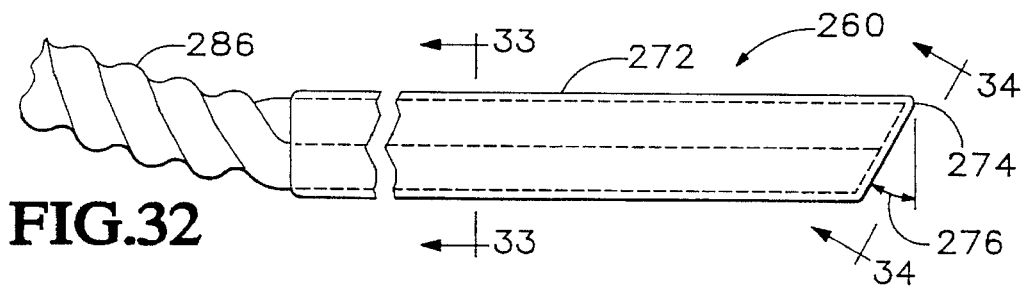
FIG.32
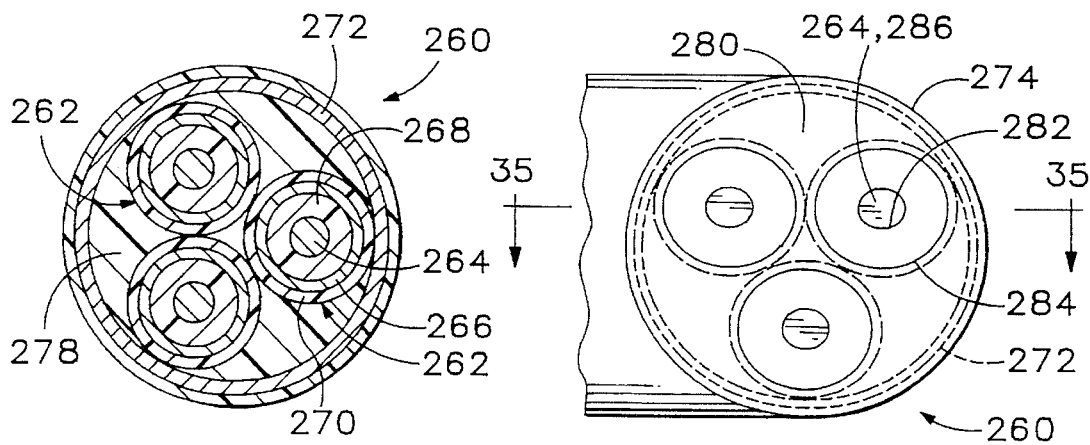
FIG.33
FIG.34

METHOD OF MAKING IMPLANTABLE MICROELECTRODE

This application is a division of Corbett, III et al. U.S. patent application Ser. No. 08/136,650, filed Oct. 14, 1993, now abandoned, which is a continuation-in-part of U.S. patent application Ser. No. 08/046,658, filed Apr. 12, 1993, now abandoned, which is a division of U.S. patent application Ser. No. 07/781,494, filed Oct. 22, 1991, now U.S. Pat. No. 5,201,903.

BACKGROUND OF THE INVENTION

The present invention relates to microelectrodes for placement within living beings to stimulate neurons electrically and to detect electrical neural activity, and relates particularly to the definition of electrode contact surfaces for such electrodes.

For several years research has been conducted in attempts to establish communication through living neurons, to communicate to the human brain information which can no longer be provided by a person's own eyes or ears, to stimulate paralyzed muscles, to stimulate autonomic nerves, as to control bladder function or pace the heart, or to control prosthetic limbs.

It is well known that electrical stimulation of certain nerves and certain regions of the brain can be perceived consciously, and research is being performed with the intention of eventually learning how to stimulate nerves in ways which can provide useful information to a person whose ability to hear or to see has been lost.

To utilize neural prostheses, electrical connections must be made to living neurons. Such connections must be made by extremely small electrodes, in order to isolate currents within small regions of living tissue. Active electrode sites can be placed very close to nerve cells, and electrical activity at the active electrode sites can be used to provide stimulation to the nerves. To limit the mechanical trauma caused by insertion and chronic presence of electrode structures, the entire electrode structure and associated wires must be as small as possible consistent with the required ability to conduct electrical energy, and must be of materials which will not react with the living body.

Implanted electrodes and conductors connected to them must be electrically insulated very effectively, because of the very small voltages and currents being utilized. The localized nature of the electrical potential gradient which must be detected by a microelectrode, and the fragility of neurons, dictate a microelectrode tip with small dimensions (typically less than 5×25 microns), which in turn produces a high impedance in the interface of metal to electrolyte. Since the probe as a whole must have a slender profile to minimize disruption of tissue, the requirement to minimize shunt losses along the insulated shank of the probe falls on a very thin dielectric coating which must be cleanly excluded from the tiny exposed tip or window. Insulating coatings on conductors must be free from pinholes and should be tightly adhered to the insulated wires and parts of electrodes. It is known that there are some biologically compatible dielectric materials which can be applied consistently and successfully as coatings of uniform thickness for such small structures as are found in microelectrodes to be used for neural prostheses. An insulating coating of Parylene-C®, a polymerized diparachloroxylyene produced by the Union Carbide Corporation, is known to have the required biological compatibility and electrical insulation qualities and can be applied successfully to electrode surfaces, but the techniques previously available for removing portions of such a coating have not been entirely satisfactory.

At the same time, active contact sites of the electrodes must be clean and must typically present as low a resistance as is possible to electrical current at their surfaces. Although current is necessarily very small, because of the need to carry current pulses to very small regions, current density is significant in the small, exposed active contact site surface of an electrode, where it is exposed to the saline environment within a living body, and the electrode must be of a corrosion-resistant material to avoid electrochemical damage to the exposed surface of the electrode or the adjacent tissue through ion migration or other mechanisms.

Microelectrode tips require well defined active electrode sites for use as stimulation electrodes. A limiting factor in producing microelectrodes to be used in stimulating and receiving information from neurons is the ability to remove small areas of insulation cleanly and accurately, leaving clean electrode contact surfaces of limited size to be exposed to neurons. Various techniques for exposing portions of an electrode have been used in the past, but it is difficult to accurately reproduce the desired tip exposure using them. Such techniques have included AC electric corona arcing, direct heating, and plasma etching. These methods have not been completely satisfactory, either because they fail to leave a cleanly and accurately exposed electrode surface, or because the remaining adjacent insulating coating does not adhere satisfactorily and tightly to the microelectrode adjacent the exposed surfaces. Mechanical removal of an insulating coating has been very time-consuming and has a high probability of damaging the tip.

Multiple conductor microelectrodes have been produced using photolithographic integrated circuit production techniques, but these are not robust enough for some applications, and are very expensive to produce in small numbers. Since they are produced as small integrated circuits they lack conductors for connection to other electrical circuitry. It is difficult to attach conductors to such devices and then protect surfaces in the vicinity of such connections to prevent undesired electrical activity when implanted.

Use of lasers to pierce dielectric coatings in preparation of microelectrodes was described by M. J. Mela in 1965 in an article entitled "Microperforation with Laser Beam in the Preparation of Microelectrodes," published in IEEE Transactions on Biomedical Engineering, Vol. BME-13, No. 2, pp. 70–76. Mela disclosed use of a red light ruby laser, which does not satisfactorily clean insulating coatings from metal surfaces, as is needed for suitably low surface resistance. That is, before the present invention it has not been known how to remove biologically compatible dielectric materials cleanly from a metal surface using a laser to produce well-defined surface areas for contact in order to achieve a well-defined surface resistance.

What is still needed, then, is a microelectrode and a method for manufacturing such a microelectrode which is suitable for chronic biological implantation, which defines contact surfaces cleanly exposed, of an accurately predetermined and controlled size and location, and surrounded by effectively and securely attached dielectric material.

SUMMARY OF THE INVENTION

The present invention provides improved microelectrodes and a method for manufacturing such microelectrodes suitable for chronic implantation in a living person to accomplish electrical stimulation of nerves and to sense electrical activity within nerves.

In accordance with the present invention a biologically implantable multiconductor microelectrode comprises a plurality of fine wires electrically insulated from each other and held together in a predetermined spatial relationship with each other by a quantity of a dielectric material through which an opening is defined to expose a predetermined area of each of such fine wires through a respective one of the openings. In some embodiments of the invention, conductive metal may be deposited and electrically connected with the surface of the respective one of the fine wires in each of the openings, presenting an exterior surface of corrosion-resistant metal having a desired conductivity.

In one embodiment of the microelectrode according to the invention several fine wires are wrapped about a support core which may be a wire or a small tube.

In another embodiment of the microelectrode of the invention, several fine wires are arranged in a generally planar array, parallel with each other, and active electrode sites are defined by openings through the dielectric material, exposing cleanly a surface of a respective wire at a respective location in the planar array.

In yet another embodiment of the invention a microelectrode assembly incorporates active electrode sites located on a substrate chip of an integrated circuit. A cable of fine wire conductors is connected to terminal pads on the substrate and leads away from the microelectrode. The entire microelectrode assembly has a coating of a biologically implantable dielectric material, and active electrode sites are located in openings cut through the coating of dielectric material by the use of a beam of ultraviolet light, as from a laser, to expose conductive material located there on the substrate.

According to the method of the invention, a biologically implantable microelectrode is prepared by directing a highly focused beam of ultraviolet light of sufficient intensity, such as a laser beam, onto a coating of dielectric material on a conductor body of an electrode, to ablate dielectric material to define an active electrode site on a portion of the electrode conductor body. In one method according to the present invention, the ultraviolet light is provided by a laser beam and is also used to briefly thermally fuse a quantity of the dielectric material located immediately adjacent the active electrode site, allowing the dielectric material to resolidify adhered to the electrode conductor body.

In a further method according to the present invention a plurality of fine wires are held together in a predetermined spatial relationship to each other by a biologically implantable dielectric material, and active electrode sites are prepared by directing a beam of ultraviolet light, as from a laser, onto predetermined locations in a distal end portion of the multiconductor microelectrode. The fine wires held together and stiffened by coatings of dielectric material to form the implantable microelectrode extend away from the microelectrode in the form of a flexible group or cable of fine wires to be connected to other electrical circuitry.

The foregoing and other objectives, features, and advantages of the invention will be more readily understood upon consideration of the following detailed description of the invention, taken in conjunction with the accompanying drawings.

BRIEF DESCRIPTION OF THE DRAWINGS

FIG. 30 is a view, taken along line 30—30 at an enlarged scale, of the distal end of the microelectrode shown in FIG. 28.

FIG. 31 is a sectional view, taken along line 31—31 of FIG. 30.

FIG. 32 is a view of a biologically implantable multiconductor microelectrode according to the present invention including bipolar active electrode sites.

FIG. 33 is a sectional view, at an enlarged scale, taken along line 33—33 of FIG. 32.

FIG. 34 is a view taken along line 34—34 of FIG. 32, at an enlarged scale, showing the active electrode sites of the microelectrode.

DETAILED DESCRIPTION OF THE INVENTION

Figure 1:
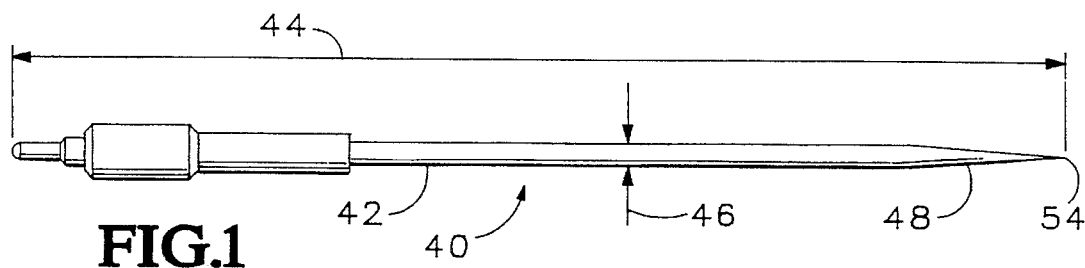
FIG. 1 is a view of a biologically implantable, single-conductor microelectrode including an active electrode site prepared according to the present invention.
Figure 2:
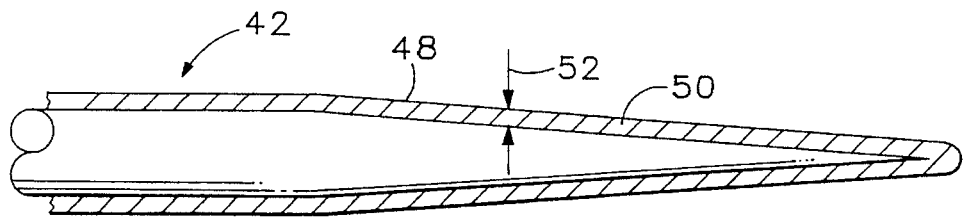
FIG. 2 is a detail view, at an enlarged scale, of the distal end of the microelectrode shown in FIG. 1 during the process of preparation of an active electrode site.
Figure 3:
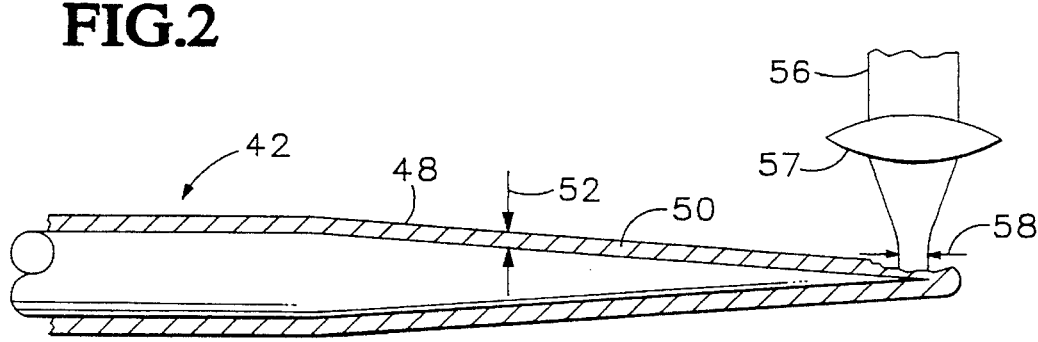
FIG. 3 is view similar to FIG. 2, showing a further stage in the process of preparation of an active electrode site.

Referring now to the drawings which form a part of the disclosure, and particularly referring to FIGS. 1–4, a microelectrode 40 having a conductor body 42 generally in the form of a straight needle of a platinum-iridium alloy or other suitable metal with a conically pointed tip, and may have a length of, for example, three inches and a diameter 46 of 0.010 inch (250 μm). The conductor body 42 has a conical distal end 48 and the body 42 including the distal end 48 is covered with a thin film coating of a dielectric material 50 which is compatible with being implanted within a living body. Dielectric materials which are useable for such a coating include fluorocarbons, polyimides or derivatives thereof, epoxies, enamel, or a polymer of para-chloroxylylene, such as that available from Union Carbide Corporation under the trademark Parylene-C®. Such dielectric materials are provided in the form of very thin film coatings, applied so as to completely cover the surfaces of the microelectrode. Such a film of dielectric material 50 has, for example, a thickness 52 of 6–12 μm of Parylene-C® vacuum deposited on the surface of the electrode conductor body 42.

An active electrode site 54 is provided at the distal end 48 of the microelectrode by ablating the coating of dielectric material 50 by exposing it to a scanned highly-focused ultraviolet laser beam 56. Preferably, for use of the electrode in providing electrical interconnection with neurons, an active electrode site about 0.001 inch (25 microns) long including the sharpened point of the electrode body is cleaned of its dielectric coating by use of such a laser beam 56, focused to a spot having a diameter 58 on the order of 25 μm.

For example, a frequency-quadrupled YAG (FQY) laser operated in the fundamental transverse electromagnetic ($TEM_{00}$) mode is suitable to ablate portions of the coating 50. Typically, this laser is Q-switched at around 1–20 KHz, producing a 40 ns full-width half maximum (FWHM) pulse which is focused by a focusing lens 57 to about a 25 μm spot, producing a fluence of approximately 1–5 joules/cm$^2$, at an average power of 10–50 milliwatts. Such a laser has a 266 nanometer wavelength which is in the ultraviolet (UV) range.

It has been found that such a highly focused laser beam in the ultraviolet frequency band is readily absorbed by the dielectric coating materials mentioned above, and that it is also absorbed by the surfaces of metals such as platinum or iridium, used as the conductor body 42 of such an electrode 40, with the result that the dielectric materials are both vaporized and photoablated, removing them cleanly from the surfaces of the metal of the electrode body 42. The mechanism by which this ablation of the dielectric material occurs is not definitely known, but it is believed to be a combination of conversion of the laser light energy to heat in the dielectric material 50 and the underlying metal, which acts primarily by evaporating the dielectric material without leaving an ash, and by some chemical dissociation of the polymeric dielectric material induced by the UV light energy. Additionally, the underlying surfaces of the metal of the electrode conductor body 42 are heated very quickly to temperatures apparently exceeding 1000° C., which vaporizes remaining polymeric dielectric material, leaving the surface of the metal clean as a relatively low resistance contact surface for a conduction of electrical current.

The FQY laser beam spot can be moved under computer software control to scan the dielectric material to remove it from the conductor body. Scanning control can be provided, for example, by equipment designed to control lasers for use in manufacture of integrated circuit products, such as is available from Electro Scientific Industries, Inc., of Beaverton, Oreg. Preferably, the UV laser is utilized together with exhaust and positive gas pressure systems to keep debris away from the focusing lens and the area where dielectric material is being ablated. Operation of the laser at the powers mentioned above provides an effective range of etch depths of approximately 1–50 microns in polyimide or Parylene-C® (polypara-chloroxylylene).

Surfaces of the dielectric material 50 remaining adjacent the active electrode site are also heated by the effects of the UV laser beam, fusing the dielectric material briefly. The dielectric material 50 resolidifies adhering tightly to the surface 60 of the metal of the conductor body of the electrode, and with a smooth exterior surface 62 exposed.

Figure 4:
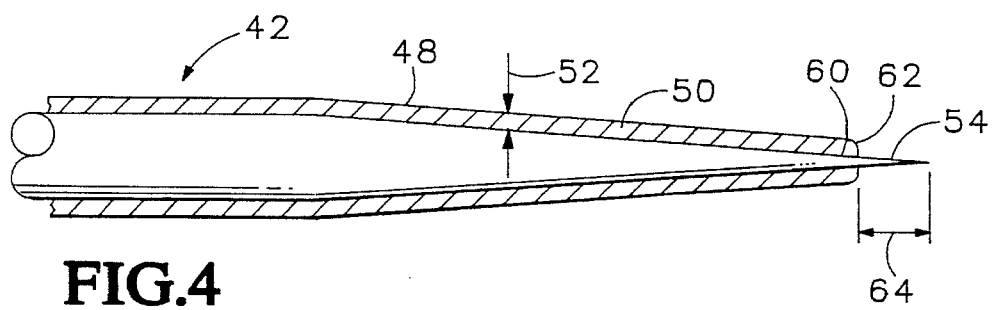
FIG. 4 is a view similar to FIG. 2, showing the completed active electrode site.
Figure 5:
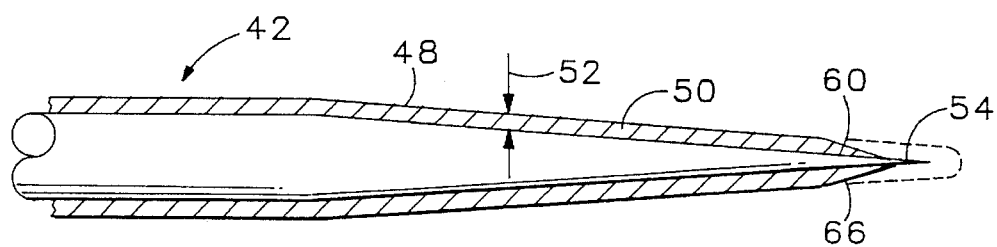
FIG. 5 is a view similar to FIG. 4, showing a detail of a microelectrode prepared according to the present invention with a somewhat different active electrode site.
Figure 6:
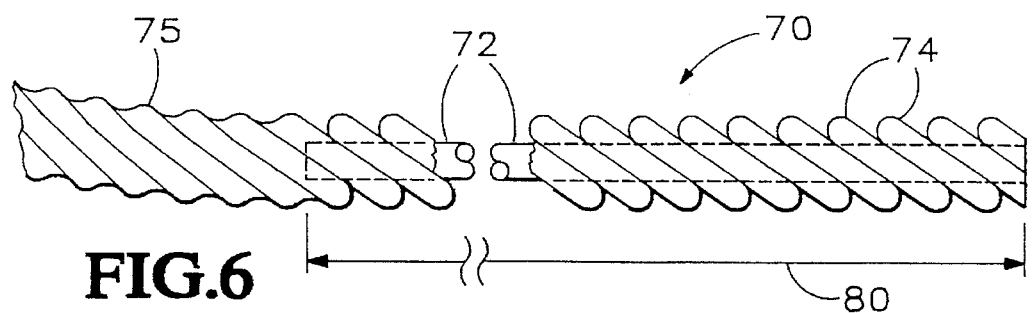
FIG 6 is a view of a biologically implantable microelectrode multiconductor according to the present invention, at an early stage of preparation, together with a portion of a stranded cable connected to the microelectrode.

As shown in FIG. 4, the dielectric material 50 may be cut sharply away leaving a full-thickness layer of dielectric material 50 adjacent the active electrode site, while as shown in FIG. 5, the remaining dielectric material 50 is tapered in the area 66 adjacent the active electrode site 54, by selectively etching to different, shallower, depths, proceeding away from the active electrode site 54, thus sculpting the microelectrode in a manner to reduce insertion trauma. Using the method of the invention, an active electrode site 54 can be prepared with an exposed sharp point having a length 64 as small as 25 μm.

A biologically implantable multiconductor microelectrode 70, shown in FIGS. 6–13, includes a core 72, which may be of solid metal similar to that used for the conductor body 42 of the implantable electrode 40 described previously, or may be of tungsten. Several extremely fine wires 74, for example, six platinum-iridium alloy wires of American Wire Gauge 52, having a wire diameter of approximately 18 μm (0.0007 inch), extend from a helically stranded multiconductor cable 75 of such wires each insulated and connected to each other by suitable coatings of flexible dielectric material (shown in the drawings with greatly exaggerated thickness for the sake of clarity). The fine wires 74 are wrapped around the solid core 72 in a helical serving in which the individual fine wires 74 lie neatly alongside one another without overlapping. Each of the wires 74 has an individual thin coating 76 (FIG. 9) of dielectric material, preferably polypara-chloroxylylene (Parylene-C®), and a further coating 78 of Parylene-C® or other dielectric material adhesively attaches the fine wires 74 to one another and to the core 72, forming a monolithic, elongate multiconductor microelectrode body having a desired length 80 of, for example, 3 cm.

Figure 7:
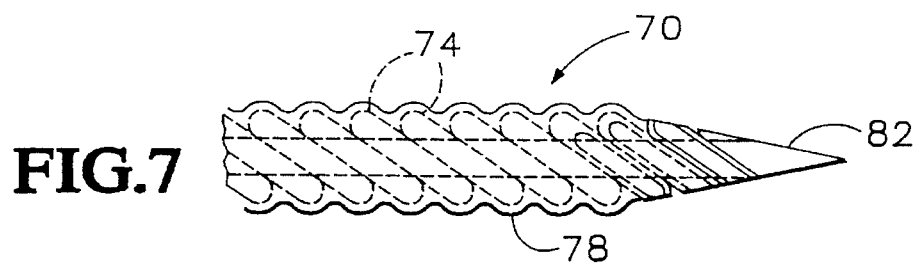
FIG. 7 is a detail view of the distal end of the microelectrode shown in FIG. 6, at a later stage of preparation.

The fine wires 74 and the core 72 are neatly cut and tapered to form a sharp conical point 82 at the end of the microelectrode 70, as shown in FIG. 7, for example, by precise abrasion, using lapidary techniques, and/or other methods including chemical etching, selective heating, laser ablation, or electrophoresis. After the distal end of the microelectrode 70 has been shaped, an additional thin coating 84 of dielectric material is added, at least over the portions of the microelectrode which have been affected by the process of forming the sharp conical point 82, again providing an insulating and completely tight coating.

Using the UV laser beam as previously described, an active electrode site 86 is provided on each of the fine wires 74 by ablating the dielectric material of the coatings 76, 78 and 84 from the wire over an area of about 250 square microns, for example, forming a circular opening 88 about 18 μm (0.0007 inches) in diameter through the dielectric material covering each of the fine wires 74. As described previously in connection with the single microelectrode 40, a shallow surface layer of the dielectric material surrounding the cleaned metal surface forming each of the active electrode sites is fused and resolidified in close adhesion to the metal surface of the fine wire, as may be seen in FIG. 9.

Figure 8:
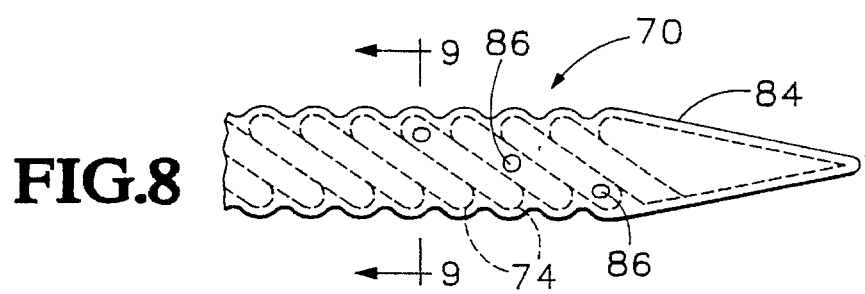
FIG. 8 is a view similar to that of FIG. 7 showing the completed microelectrode.
Figure 9:
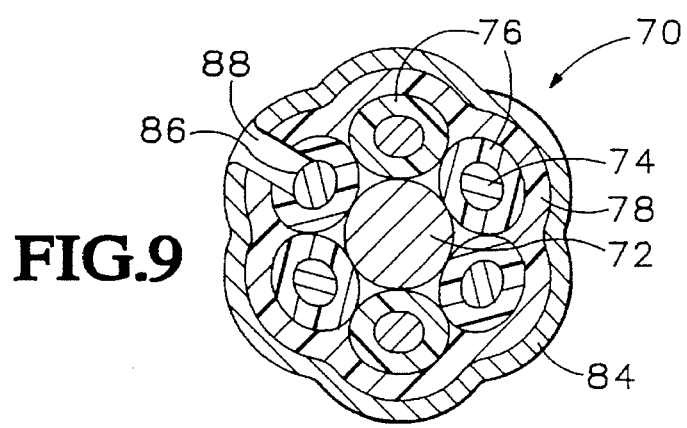
FIG. 9 is a section view taken along line 9—9 of FIG. 8.
Figure 10:
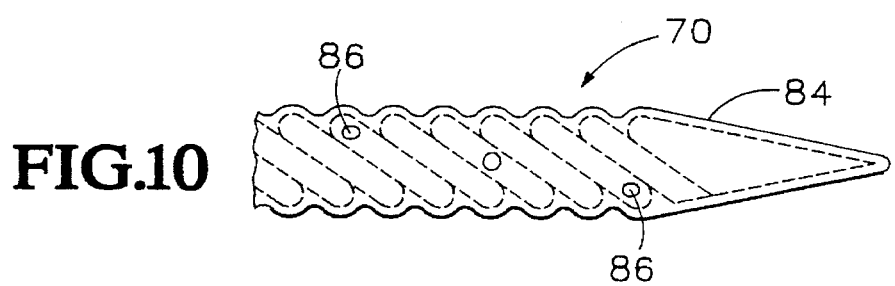
FIG. 10 is a view similar to that of FIG. 8, showing a microelectrode which is a slightly different embodiment of the invention.

The spacing and orientation of the active electrode sites 86 corresponding to the several fine wires 74 may be chosen as desired consistent with the pitch of the helical wrapping of the fine wires about the core. When desired, the active electrode sites 86 may be spaced radially about the multiconductor microelectrode 70, or, as shown in FIGS. 8 and 10, they may be spaced longitudinally in a helical arrangement along the microelectrode 70, separated more or less from one another as determined by the number of adjacent ones of the fine wires 74 which are skipped between consecutive active contact sites 86 defined along the microelectrode 70.

Figure 11:
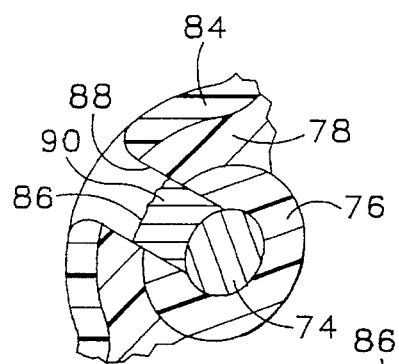
FIG. 11 is a view of a portion of FIG. 9, at a further enlarged scale, showing an active electrode site including a deposit of conductive material within an opening through a coating of dielectric material.
Figure 12:
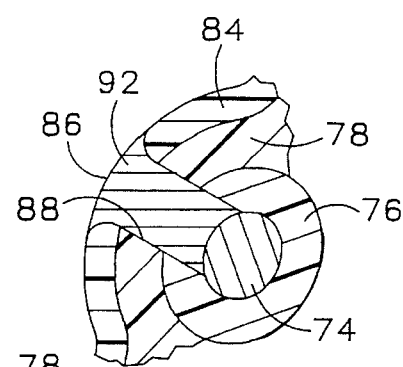
FIG. 12 is a view similar to FIG. 11, showing an active electrode site including a deposit of conductive material flush with an outer surface of a dielectric material surrounding a conductor.
Figure 13:
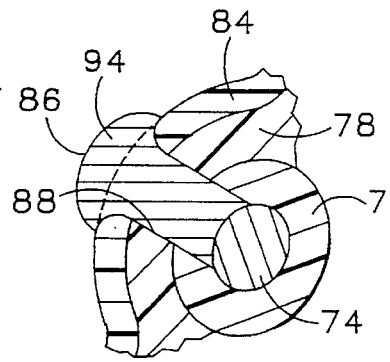
FIG. 13 is a view similar to FIG. 11, showing an active electrode site including a deposit of conductive material protruding beyond an outer surface of surrounding dielectric material.
Figure 14:
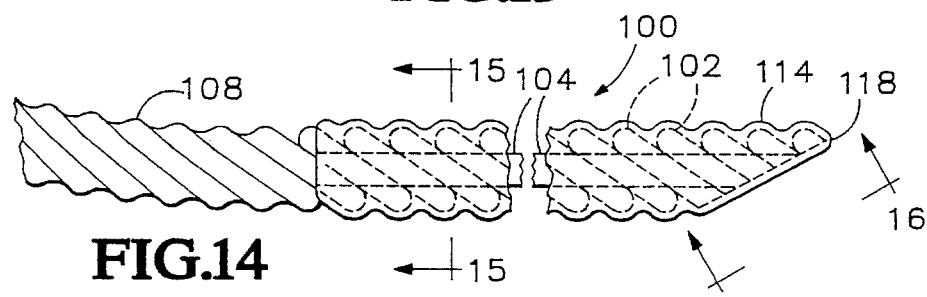
FIG. 14 is a view of a biologically implantable multiconductor microelectrode which is another embodiment of the invention, together with a portion of a multiconductor cable connected thereto.
Figure 15:
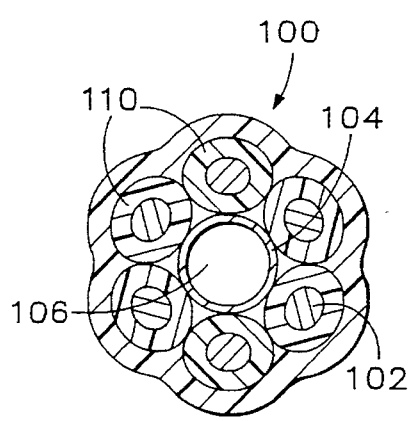
FIG. 15 is a sectional view taken along line 15—15 of FIG. 14, at an enlarged scale.
Figure 16:
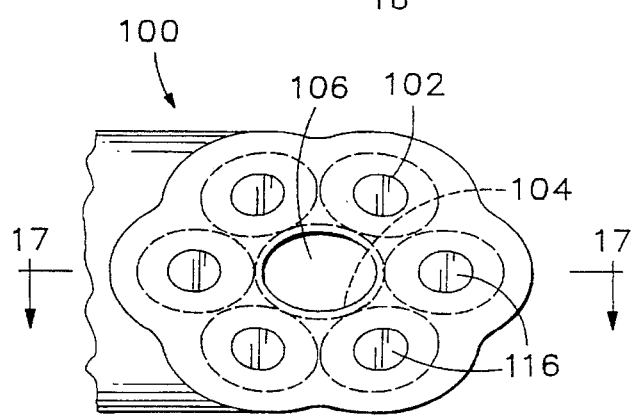
FIG. 16 is a view of a beveled end surface of the microelectrode shown in FIG. 14, taken in the direction indicated by the line 16—16.
Figure 17:
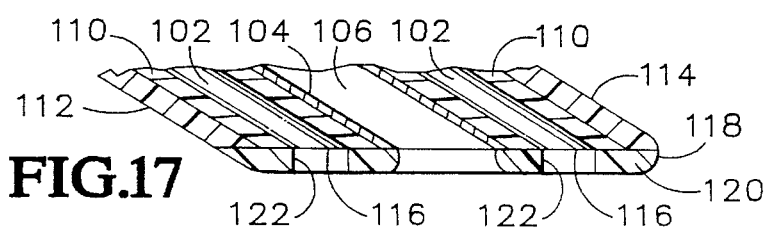
FIG. 17 is a sectional view of a detail of the microelectrode shown in FIG. 14, taken along the line 17—17 of FIG. 16.

Depending upon the intended use of the microelectrode, the openings 88 of the active electrode sites 86 may be left as depressions relative to the outer surface of the outer coating 84 or 78 of dielectric material, or suitable deposits of metal having desired conductivity and resistance to electrochemical corrosion-resistant may be provided electrophoretic deposition, with such deposits attached to and electrically interconnected to the cleaned surface of the fine wire 74, either partly filling the openings 88 defined through the dielectric material, as with the deposit 90 shown in FIG. 11, filling the opening flush with the outer surface of the dielectric material, as with the deposit 92 shown in FIG. 12, or forming a small bump standing proud above the outer surface of the dielectric material, as with the deposit 94 shown in FIG. 13.

Where a core 72 of wire is not desired a quantity of the dielectric material may be deposited at the distal end of the multiconductor microelectrode and shaped to the desired tip configuration.

The several fine wires continue away from the electrode, and may be held together as a helical strand or, depending upon the application, may be held together in a planar ribbon cable form to a desired length for connection through use of connectors (not shown) to electric equipment associated with use of the microelectrode 70 described herein.

A biologically implantable multiconductor microelectrode 100 somewhat similar to the microelectrode 70 is shown in FIGS. 14–17 and also has a plurality of conductors such as fine wires 102 formed into a helical serving, about either a solid core (not shown) or a thin-walled tube 104 to define a lumen 106 within the microelectrode 100. The fine wires 102 are extensions of the conductors of a slender multiconductor cable 108 similar to the cable 75 described previously. The individual fine wires 102 have respective coatings 110 of a biologically implantable dielectric material, and have been overcoated by a coating 112 of similar dielectric material to hold them together in the desired helical form attached to the tube 104. The distal end 114 of the microelectrode is cut along a plane extending obliquely with respect to the central longitudinal axis 116 of the electrode to form a beveled point 118, as by the use of lapidary techniques with the microelectrode held potted in a body of material which can later be removed. For example the electrode may be potted or held firmly attached to a substrate, such as a glass slide, to stiffen it and facilitate the cutting process. The material holding the microelectrode to the substrate could be Aremco Crystal Bond 509, a thermoplastic microcrystalline wax-based adhesive available from Aremco Products, Inc. of Ossining, N.Y. This material may later be removed by solution in acetone, which does not dissolve the Parylene-C® dielectric material, with optional application of heat to make the process more rapid. After the beveled point 118 is formed, an additional layer 120 of similar dielectric material is applied to the distal end 114 of the multiconductor microelectrode. An active electrode site 116 is defined, by using a UV laser as previously described to ablate the dielectric material of the layer 120 and form openings 122 having the desired size, which may be similar to that of the active electrode sites 86 described previously, on the end of each of the fine wires 102 as they are presented on the beveled surface of the distal end 114 of the microelectrode.

The active electrode sites 116 may each, as described above in connection with the microelectrode 70, also be partly or fully filled with a deposit (not shown) of a desired metal electrophoretically deposited onto the surface of the fine wire 102 to provide partial filling of the opening 122, to fill the opening 122 flush with the outer surface of the dielectric material, or to provide a small bump standing proud above the outer surface of the dielectric material of the layer 120.

Figure 18:
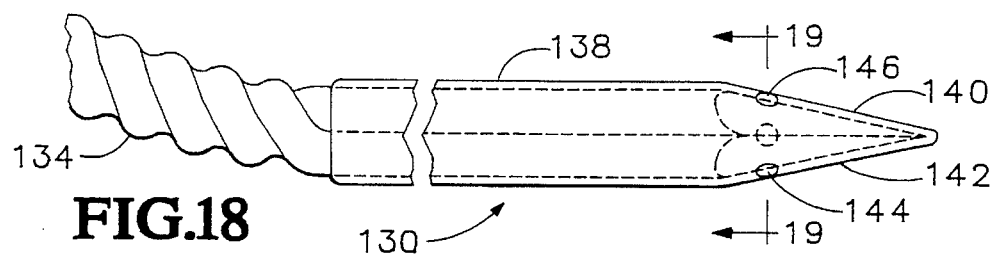
FIG. 18 is a view of a biologically implantable multiconductor microelectrode which is yet a further embodiment of the present invention, together with a portion of a multiconductor cable connected thereto.
Figures 19, 21:
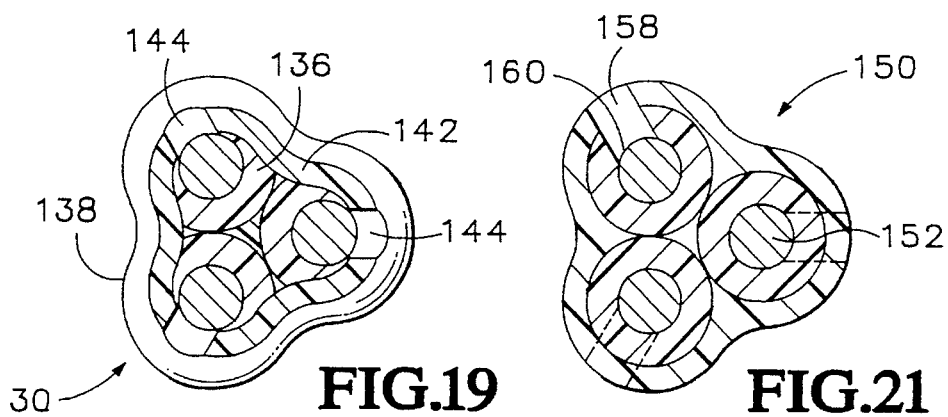
FIG. 19 is a sectional view, taken along line 19—19 of FIG. 18, at an enlarged scale.
FIG. 21 is a sectional view, taken along line 21—21 of FIG. 20, at an enlarged scale.

A biologically implantable multiconductor microelectrode 130, shown in FIGS. 18 and 19 includes three straight, parallel fine wires 132, which are continuations of the several conductors of a cable 134. Each of the fine wires 132 is coated individually with a layer 136 of biologically implantable dielectric material. The three fine wires 132 are held together as a group by an adhesive overcoating 138 of similar dielectric material. The dielectric material may, both for the individual coatings 136 on the fine wires 132 and for the additional material holding the coated wires 132 together, be one of the types of materials mentioned previously in connection with the electrode 40. In some cases it may also be desirable to add a further coating (not shown) of dielectric material such as an epoxy or enamel over all or part of the length of the microelectrode 130 to add mechanical stiffness to the microelectrode 130, in order to facilitate insertion through tissue surrounding a nerve.

A distal end 140 of the microelectrode 130 is sharpened into a generally conical point using lapidary techniques, after which an additional coating 142 of dielectric material is applied to at least the distal end portion of the microelectrode 130 to provide a tightly adhered impervious coating covering the entire microelectrode 130. Thereafter, openings 144 are formed by use of an ultraviolet laser beam in the manner described previously, providing three active electrode sites 146 located close together on the tapered point portion of the distal end 140 of the microelectrode 130. Use of the UV laser to form the openings 144 affords accurate control over the size of each active electrode site 146, so that a desired impedance will be provided uniformly at each active electrode site 146.

As mentioned above previously in connection with the microelectrodes 770 and 100, additional conductive material can be electrophoretically deposited in contact with the fine wires 132 to build up the active electrode sites within the openings 144 formed in the dielectric material by the UV laser, so that the available contact surface area of the active electrode sites 146 may be located slightly below, flush with, or proud above the outer surface of the dielectric material of the outer coating 142 on the distal end 140.

Figure 20:
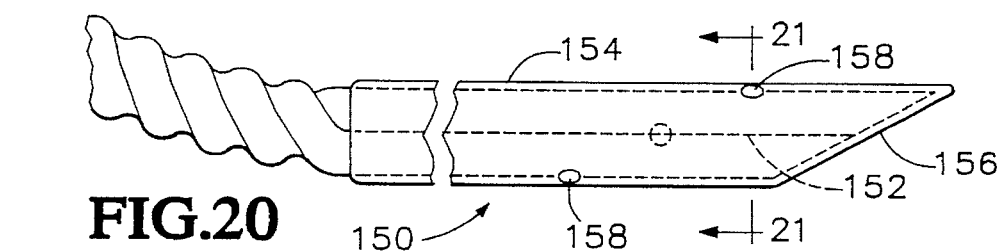
FIG. 20 is a view of a biologically implantable multiconductor microelectrode which is yet a further embodiment of the present invention, together with a portion of a multiconductor cable connected thereto.

A multiconductor microelectrode 150 shown in FIGS. 19 and 20 is similar to the microelectrode 130 just described, in that it includes several straight fine wires 152, parallel with each other and insulated from and held parallel with each other by dielectric material. An additional external coating of dielectric material may also be utilized to provide structural support, stiffening the electrode. The distal end 156 of the microelectrode is sharpened by being cut at a bevel angle, as may be accomplished by potting the distal end 156 of the microelectrode and using lapidary techniques, to form the shape shown in FIG. 20. Thereafter a final coating 154 of dielectric material is applied and a UV laser is utilized as previously described to define openings 158 through the layers of dielectric material to provide an active electrode site 160 on each of the fine wires of the microelectrode. Such active electrode sites 160 may, as illustrated in FIG. 20, be spaced apart from one another longitudinally of the microelectrode 150, although they could all be located at the same position longitudinally of the microelectrode 150.

It will be understood that deposits of metal of appropriate conductivity and resistance to electrochemical corrosion may be electrophoretically deposited on each of the active electrode sites 160 of the microelectrode 150 as described previously with respect to other microelectrodes according to the invention.

It will also be understood that as few as two fine wires 152, or four or more fine wires 152, may be grouped together, extending parallel with one another and held together by dielectric coatings as a microelectrode 130 or 150.

Figure 22:
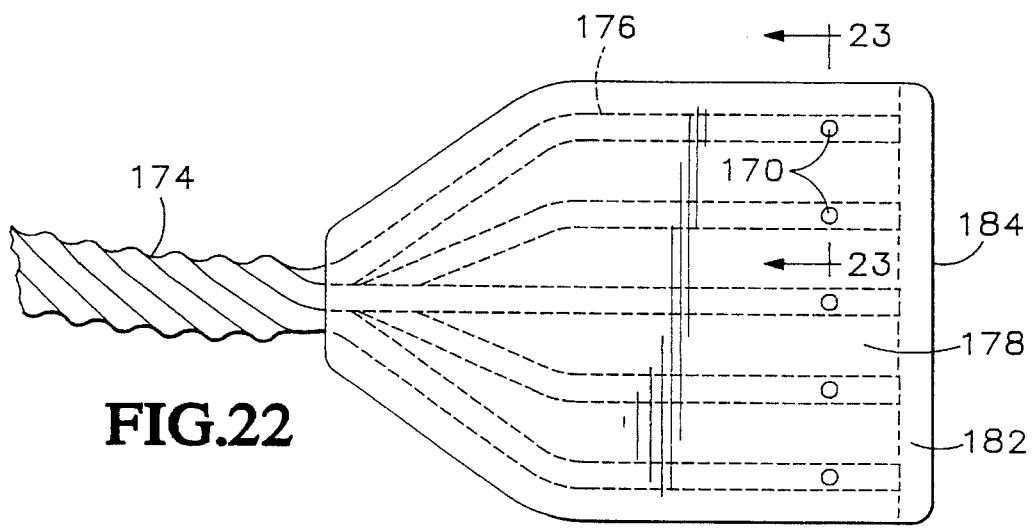
FIG. 22 is a plan view of a biologically implantable multiconductor microelectrode which is yet a further embodiment of the present invention.
Figure 23:
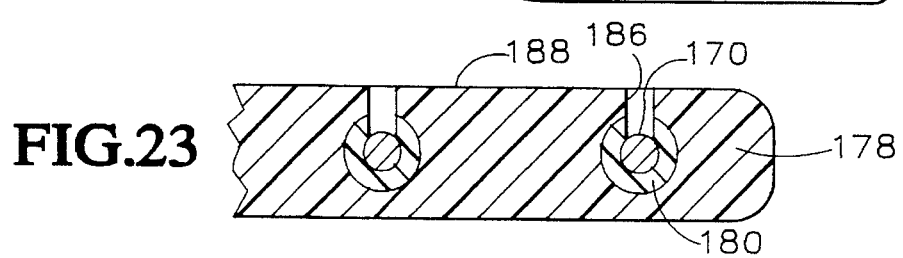
FIG. 23 is a sectional view of a detail of the microelectrode shown in FIG. 22, taken along line 23—23 at an enlarged scale.

For use in situations where a surface contact with a nerve is desired, a generally planar array of active electrode sites 170 of a biologically implantable multiconductor microelectrode 172, shown in FIGS. 22 and 23 according to the present invention may be provided in connection with a biologically implantable cable 174 similar to that disclosed in Corbett, III, et al. U.S. Pat. No. 5,201,903, of which the disclosure is hereby incorporated herein by reference. A helically stranded multiconductor cable 174 of fine wires 176 extends to the microelectrode 172, which has a generally planar body 178 including a quantity of dielectric material surrounding and supporting each of the wires 176, which are preferably coated individually with a layer 180 of dielectric material. The wires 176 are fanned out from one another in the planar body 178 to lie parallel with and spaced apart from one another by a desired pitch which may be a distance such as 150 μm (6 mils). A layer 182 of dielectric material is added to the distal end 184 of the microelectrode body 178 to insulate the distal end of each fine wire 176. Active electrode sites 170 are provided by forming openings 186 through the dielectric material of the body 178 and the layer 180 surrounding each fine wire 176 with the use of an ultraviolet laser as previously described to provide a clean contact surface area of a predetermined size on each of the fine wires 176. The placement of the active electrode sites 170 on the microelectrode 172 may be chosen to correspond with the requirements for use of the microelectrode.

Additional electrically conductive materials may be deposited in the openings 186, in contact with the exposed surfaces of the fine wires 176 to provide the desired location of the eventual contact surface of the active electrode sites 170 with respect to the outer surface 188 of the planar body 178 surrounding the fine wires 176.

Figure 24:
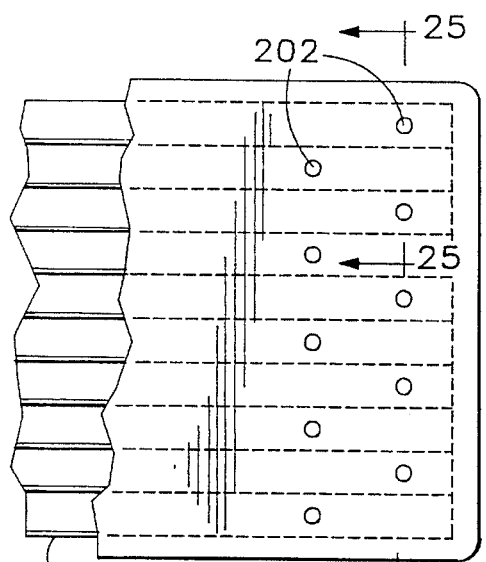
FIG. 24 is a view of a biologically implantable multiconductor microelectrode according to the present invention, embodied in a ribbon-cable.
Figure 25:
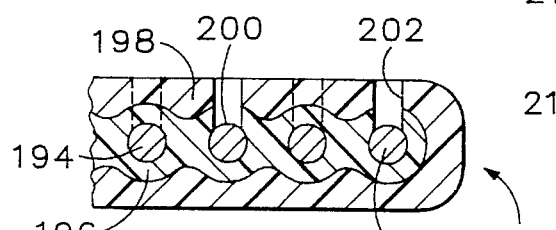
FIG. 25 is a sectional view, taken along line 25—25 at an enlarged scale, of a detail of the microelectrode shown in FIG. 24.

In yet a further alternative embodiment of the present invention, shown in FIGS. 24 and 25, a biologically implantable multiconductor microelectrode 190 according to the present invention may be formed at a distal end of a ribbon cable 192 in which several fine wires 194 are held closely together side-by-side in a ribbon-like configuration by a coating of dielectric material 196 surrounding each of the fine wires 194 and holding the several wires 194 together parallel but spaced apart slightly from each other. A further coating 198 of dielectric material is provided at the distal end of the ribbon-cable 192, and active electrode sites 200 are prepared by using a UV laser, as previously described, to provide openings 202 through the layers 196, 198 of dielectric material, exposing a predetermined small area of the surface of each of the several fine wires 194.

Figure 26:
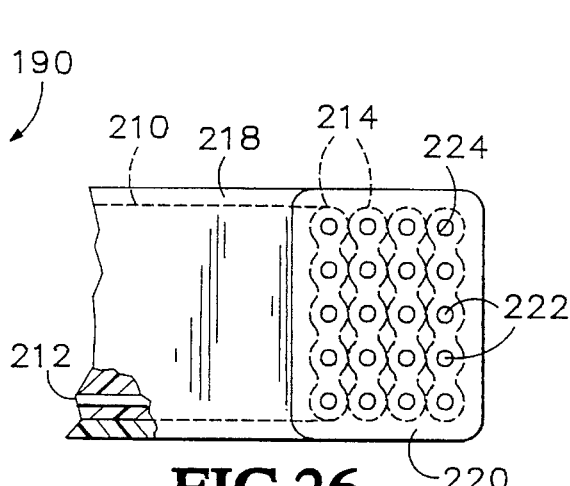
FIG. 26 is a front view of a biologically implantable multiconductor microelectrode according to the present invention, including an array of active electrode sites.
Figure 27:
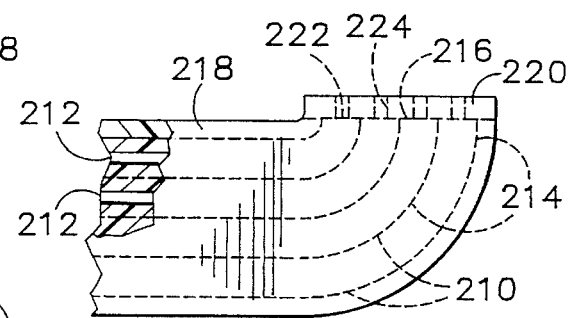
FIG. 27 is a side view of the microelectrode shown in FIG. 26.
Figure 28:
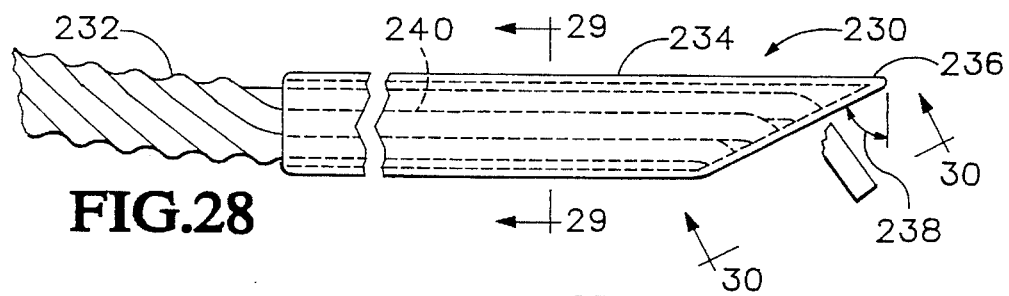
FIG. 28 is a view of a biologically implantable multiconductor microelectrode according to the present invention including a tubular needle, together with a portion of a multiconductor cable connected thereto.
Figure 29:
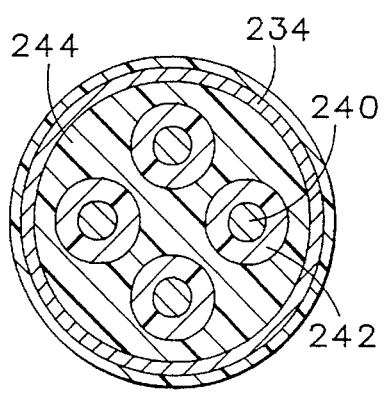
FIG. 29 is a section view, taken along line 29—29 at an enlarged scale, of the microelectrode shown in FIG. 28.
Figure 35:
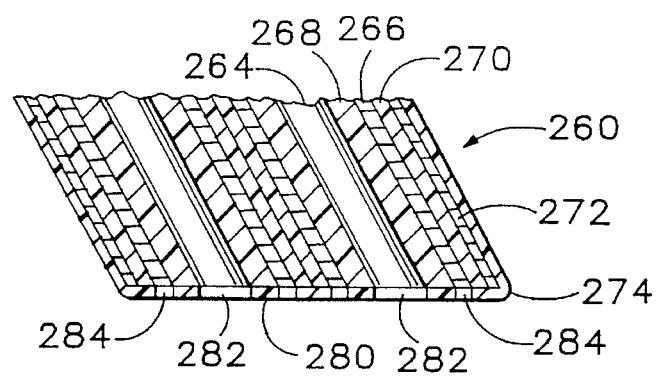
FIG. 35 is a sectional view taken along line 35—35 of FIG. 34.

Similarly, as shown in FIGS. 26 and 27, several ribbon-cables 210 of fine wires 212 may be arranged parallel with one another, with a distal end portion 214 of each separate ribbon-cable 210 bent, so that the respective fine wires 212 extend generally normal to the length of the several ribbon-cables at a contact area face 216. The several ribbon-cables 210 are held together by a coating 218 of dielectric material, and the contact area face 216, prepared by lapidary techniques, for example, exposes a distal end of each of the fine wires 212. A final coating 220 of biologically implantable dielectric material is applied to the face 216. An active electrode site 222 for each of the fine wires 212 is prepared by using an ultraviolet laser as described previously to form a respective opening 224 extending through the coating 220 of dielectric material to expose the surface of the distal end of each fine wire 212. A deposit of additional electrically conductive metal (not shown) may be electrophoretically formed on the exposed surface of each fine wire 212 as previously described.

Yet a further embodiment of the invention is a biologically implantable multiconductor microelectrode 230, shown in FIGS. 28–31, in which mechanical support for the electrical conductors extending as continuations of a multiconductor is provided by a thin-walled tubular metal needle 234. The distal end 236 of the needle is cut at a bevel angle 238, preferably 65° or greater. Several fine wires 240, each covered by a tightly adhered thin coating 242 of a biologically compatible dielectric material such as one of those mentioned previously herein, extend through the tubular needle 234 to the distal end and are held in place within the lumen of the tubular needle by being potted in dielectric material 244. A potting material suitable for securing the coaxial conductor pairs within the hollow needle is available under the trade name EPO TEK 301 from Epoxy Technologies, Inc. of Billerica, Mass. Preferably each of the fine wires 240 is bent toward the plane 246 defined by the beveled surface of the distal end 236 of the needle, to establish the location of the end of the wire 240 where desired and to present a small active electrode site surface area when the fine wires are cut to expose them as shown in FIG. 30.

Depending upon the spacing required and the impedance required of the active electrode site, an additional coating 248 of dielectric material may be applied over the beveled surface after it has been cut and polished. A UV laser beam may then be used as previously described herein to form openings 250 through the layer of dielectric material and expose a clean contact surface area for each active electrode site 252 on the microelectrode, in order to control more precisely the location and size of each active electrode site 252 defined.

In a biologically implantable multiconductor microelectrode 260 which is a slightly different embodiment of the invention, shown in FIGS. 32–35, a small number of coaxial conductor pairs 262, each including a center conductor 264, a shield conductor 266 which may be of a served wire or foil, a quantity of dielectric material 268 between the center conductor 264 and the shield 266, and an outer jacket 270 of dielectric material, extend through the lumen of a tubular needle 272 having a beveled distal end 274 which may be cut at a shallow angle 276 of, for example, 30°. The coaxial conductor pairs 262 are held fixedly located within the lumen of the tubular needle 272 by potting material 278 such as that previously described, and are cut flush with the beveled surface at the distal end 274 of the needle 272.

The beveled surface may then be covered by a final coating 280 of dielectric material, after which openings 282 are prepared by use of a UV laser beam controlled as previously described to provide a clean contact surface area 286 of a desired size in each of the desired active electrode sites to connect with the center conductor 264 of each coaxial pair. Similarly, the UV laser is used to create a circular groove 284 through the coating 280 to expose the shield conductor 266 of each coaxial pair 262, thus providing bipolar active electrode sites each having a desired electrical field characteristic made possible by the coaxial conductor pairs. Thereafter, both the center conductor 264 and shield conductor 266 of the coaxial pairs 262 may, if desired, be built up by deposits of metal to provide the actual contact surfaces of each active electrode site. It will be understood that at the proximal end of the tubular needle the coaxial conductor pairs may be held together as a flexible cable 286 of conductors extending to a suitable connector (not shown).

Figure 36:
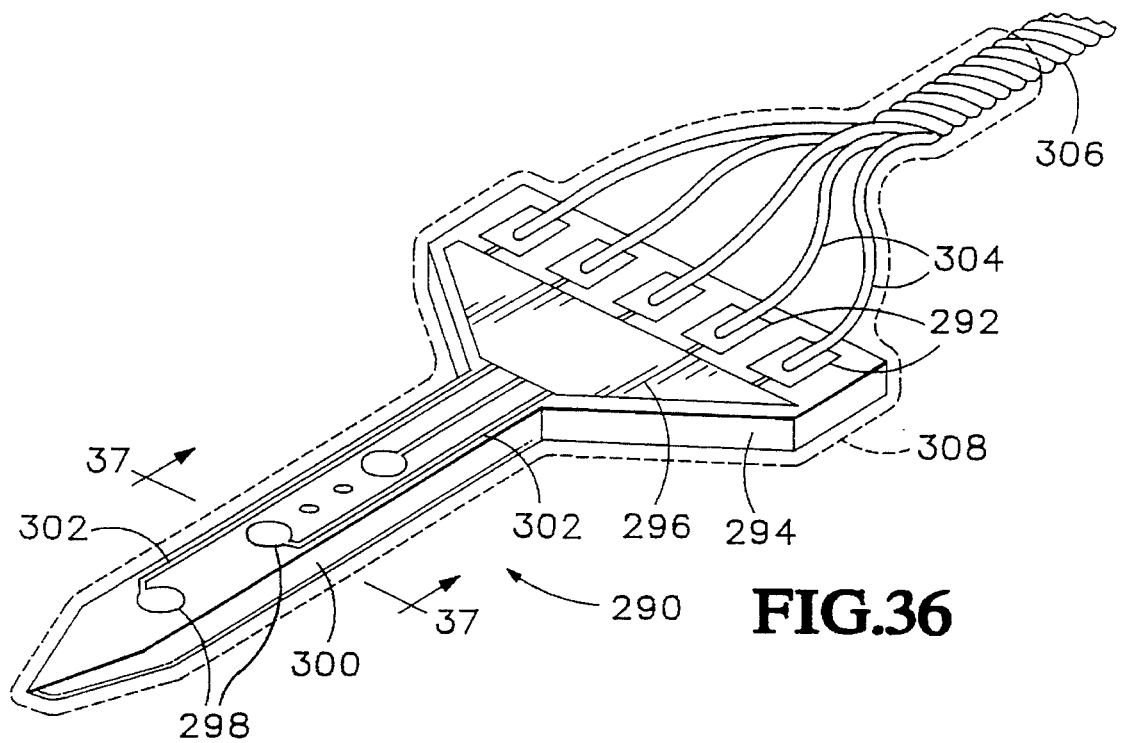
FIG. 36 is a view of a biologically implantable multiconductor microelectrode incorporating a microscopic integrated circuit, together with a part of a multiconductor cable, prepared in accordance with the present invention.
Figure 37:
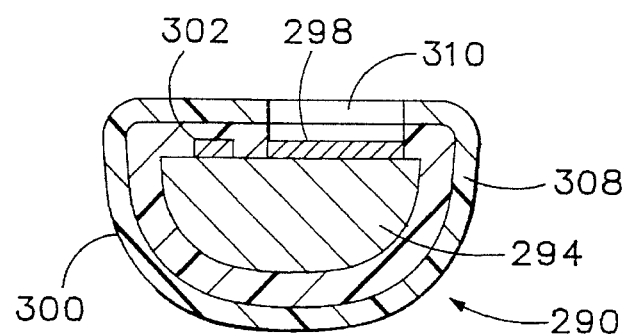
FIG. 37 is a sectional view, taken along line 37—37, of the microelectrode shown in FIG. 36.

As shown in FIGS. 36 and 37, a biologically implantable multiconductor microelectrode 290 is a tiny integrated circuit chip produced by solid state semiconductor production techniques to define several terminal pads 192 on a substrate wafer 294. An integrated circuit 296, not shown in detail, is connected to the terminal pads 292. Several active electrode sites 298 are located on a long narrow probe tip 300 small enough to be placed in a nerve, and interconnect lines 302 extend from the integrated circuit to the electrode sites 298.

Extremely fine individually insulated wires 304 are connected to the terminal pads 292 and are stranded to form a cable 306 leading away from the microelectrode 290 and may be held together by an outer coating of dielectric material (not shown). An overall coating 308, several microns thick, of a biologically compatible and implantable dielectric material, such one of those described previously herein, covers the entire microelectrode 290 and the interconnection to it of the several wires 304, to protect the microelectrode 290 and the cable 306 as an integral assembly once it has been implanted.

In order to communicate by electrical impulses between the microelectrode 290 and a nerve, each of the active electrode sites 298 is exposed through an opening 310 prepared in accordance with the method of the invention by ablating the overlying dielectric material through the use of intense ultraviolet light as from a UV laser in the manner previously described. This produces precisely located electrode sites 298 of precise size on which additional metal may be deposited if desired to raise the electrode site flush with or protruding above the coating 308. The dielectric material of the coating 308 is tightly adhered to the probe tip 300, including a layer of dielectric material 312, if any, surrounding the electrode site 298, as a result of brief thermal fusing and resolidification of a surface layer of the coating 308, as described previously with respect to the microelectrode 40.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A method of manufacturing a biologically implantable multiconductor electrode, comprising:

(a) providing a plurality of fine wires;

(b) holding said fine wires in predetermined spatial relationship to each other while applying a coating of a biologically implantable dielectric material thereto, thereby forming a distal end portion of said multiconductor electrode;

(c) arranging respective portions of all of said plurality of fine wires in a helical strand and holding said portions of said wires in a configuration defining said helical strand by said coating of dielectric material on said distal end portion thereof; and (d) directing a beam of ultraviolet light onto a predetermined location in said distal end portion, thereby ablating a portion of said dielectric material from one of said fine wires, exposing cleanly a surface area of said one of said fine wires as an electrode site while leaving said dielectric material attached securely to said fine wire adjacent said active electrode site.

2. The method of claim 1, including the steps of sharpening said distal end portion and thereafter applying a second coating of dielectric material to said helical strand of conductors before directing said beam of ultraviolet light onto said predetermined area.

3. The method of claim 2, including the step of directing said beam of ultraviolet light onto a plurality of areas of said multiconductor electrode and thereby removing a quantity of said dielectric material from each of said conductors at respective active electrode sites spaced apart from one another longitudinally of said helical strand.

4. The method of claim 1, including the further step of providing and connecting electrically to said surface area of said active electrode site on said fine wire a respective quantity of electrically conductive material and thereby replacing at least a portion of said dielectric material which has been ablated therefrom.

5. The method of claim 1, including the further step of depositing onto said surface area of said active electrode site on said fine wire a respective quantity of electrically conductive material and thereby replacing a portion of said dielectric material which has been ablated therefrom.

6. The method of claim 5 wherein said dielectric material has an outer surface, including the step of depositing said electrically conductive material onto said surface area of said active electrode site on said fine wire to a predetermined height with respect to an outer surface of said dielectric material.

7. The method of claim 1, including the additional step of shaping said dielectric material into a sharp point at said distal end of said multiconductor electrode.

8. The method of claim 1, including the additional step of thermally fusing a part of said dielectric material adjacent said surface area from which said dielectric material has been removed by said beam of ultraviolet light and resolidifying said dielectric material adhered to said wire.

9. The method of claim 1 wherein said dielectric material is a polymer of para-chloroxylylene and said beam of ultraviolet light is a laser beam.

10. The method of claim 1 wherein said step of directing a beam of ultraviolet light includes directing a narrowly focused laser beam successively onto respective portions of said dielectric material and thereby removing said dielectric material progressively.

11. The method of claim 1 wherein said step of holding said fine wires includes placing said fine wires in a support tube, providing an open distal end of said support tube, and separately exposing a respective surface area as an active electrode site on each of said fine wires, at respective locations spaced apart from one another proximate said open distal end.

12. A method of making a miniature multiconductor electrical cable including a microelectrode, comprising:

(a) coating a plurality of fine elongate electrical conductors with a first continuous layer of a first insulating material;

(b) arranging respective intermediate portions of all of said plurality of fine elongate electrical conductors closely adjacent one another;

(c) placing and holding a respective terminal portion of each of said fine elongate electrical conductors in a fixture in a terminal configuration with said terminal portions of said conductors substantially parallel with one another and spaced apart from one another in a planar arrangement at a predetermined pitch;

(d) ribbonizing said terminal portions of said fine elongate electrical conductors by applying and curing a layer of insulating ribbonizing material over said terminal portions, embedding said terminal portions in said material and thereby holding said terminal portions in a terminal configuration; and (e) stripping away said layers of insulating material from each of said fine elongate electrical conductors in a portion of said ribbonized portion of said cable by use of an ultraviolet laser beam scanned in an appropriate pattern under computer control while holding said conductors arranged with said predetermined pitch therebetween adjacent said terminal portion of each of said conductors to provide an opening cleanly exposing a surface area of each said electrical conductor as an active electrode site with a predetermined configuration in a terminal portion of said cable.

* * * * *